(12) United States Patent
Leconte et al.

(10) Patent No.: US 9,244,020 B2
(45) Date of Patent: Jan. 26, 2016

(54) METHOD AND DEVICE FOR DETECTING DEFECTS IN MATERIAL DISTRIBUTION IN TRANSPARENT CONTAINERS

(75) Inventors: Marc Leconte, Loire sur Rhone (FR); Guillaume Bathelet, Marcy l'Etoile (FR)

(73) Assignee: MSC & SGCC, Vourles (FR)

( * ) Notice: Subject to any disclaimer, the term of this patent is extended or adjusted under 35 U.S.C. 154(b) by 98 days.

(21) Appl. No.: 13/985,965

(22) PCT Filed: Feb. 16, 2012

(86) PCT No.: PCT/FR2012/050339
§ 371 (c)(1),
(2), (4) Date: Oct. 14, 2013

(87) PCT Pub. No.: WO2012/110749
PCT Pub. Date: Aug. 23, 2012

(65) Prior Publication Data
US 2014/0029019 A1    Jan. 30, 2014

(30) Foreign Application Priority Data
Feb. 18, 2011 (FR) ...................................... 11 51363

(51) Int. Cl.
*G01B 11/06* (2006.01)
*G01N 21/90* (2006.01)
*G01N 21/958* (2006.01)

(52) U.S. Cl.
CPC .............. *G01N 21/958* (2013.01); *G01B 11/06* (2013.01); *G01B 11/0691* (2013.01); *G01N 21/90* (2013.01)

(58) Field of Classification Search
CPC .... G01B 11/06; G01B 11/0691; G01B 11/08; G01B 11/105; G01B 11/12; G01B 11/2408; G01B 11/25; G01B 11/272; G01N 21/90; G01N 21/958

USPC ........................................................ 356/239.4
See application file for complete search history.

(56) References Cited

U.S. PATENT DOCUMENTS 3,807,870 A * 4/1974 Kalman ...................... 356/630
3,942,001 A * 3/1976 O'Connor ................. 250/223 B
(Continued)

FOREIGN PATENT DOCUMENTS

DE    10 2008 01884    10/2009
EP    0 320 139    6/1989
(Continued)

*Primary Examiner* — Gregory J Toatley
*Assistant Examiner* — Jarreas C Underwood
(74) *Attorney, Agent, or Firm* — Clark & Brody

(57) ABSTRACT

An inspection process for detecting defects of thin type, on transparent containers for a series of inspection points distributed over an inspection region superposed according to a determined height of the container taken according to central axis thereof, and according to the circumference of the container comprising:
  sending a light beam so as to recover on a light sensor the reflected beams by the internal and external faces of the wall of the container,
  measuring at each inspection point the thickness of the wall as a function of separation at the level of the light sensor between the reflected beams by the internal and external faces,
  processing the thickness measurements by analyzing their distribution over the inspection region to extract therefrom geometric characteristics, and comparing these geometric characteristics to reference values to determine if the container has a material distribution defect.

22 Claims, 4 Drawing Sheets

(56) References Cited

U.S. PATENT DOCUMENTS

| | | | |
|---|---|---|---|
| 3,984,498 A * | 10/1976 | McChesney et al. | 525/230 |
| 3,994,599 A * | 11/1976 | Southwell | 356/504 |
| 4,160,385 A * | 7/1979 | Gromlich et al. | 73/622 |
| 4,337,025 A * | 6/1982 | Pagels et al. | 425/392 |
| 4,859,861 A * | 8/1989 | Mersch | 250/559.22 |
| 4,888,824 A * | 12/1989 | Andersen et al. | 324/668 |
| 4,902,902 A * | 2/1990 | Tole | 250/559.28 |
| 5,118,954 A * | 6/1992 | Grosso | 250/559.24 |
| 5,289,265 A * | 2/1994 | Inoue et al. | 356/632 |
| 5,291,271 A * | 3/1994 | Juvinall et al. | 356/632 |
| 5,657,124 A * | 8/1997 | Zhang et al. | 356/485 |
| 6,285,451 B1 * | 9/2001 | Herron | 356/630 |
| 6,806,459 B1 * | 10/2004 | Ringlien et al. | 250/223 B |
| 6,975,410 B1 * | 12/2005 | Sturgill | 356/631 |
| 7,385,174 B2 * | 6/2008 | Ringlien | 250/223 B |
| 7,385,710 B1 * | 6/2008 | Sturgill | 356/632 |
| 7,924,421 B2 * | 4/2011 | Schmidt et al. | 356/239.4 |
| 8,208,141 B2 * | 6/2012 | Schmidt et al. | 356/402 |
| 8,593,515 B2 * | 11/2013 | Detrois et al. | 348/127 |

FOREIGN PATENT DOCUMENTS

| | | |
|---|---|---|
| EP | 0 584 673 | 3/1994 |
| EP | 0 871 007 | 10/1998 |
| EP | 1 795 862 | 6/2007 |
| FR | 2 798 995 | 3/2001 |
| GB | 2 195 178 | 3/1988 |
| JP | 06-201336 | 7/1994 |
| JP | 2007-155393 | 6/2007 |
| JP | 2008-506111 | 2/2008 |

* cited by examiner

METHOD AND DEVICE FOR DETECTING DEFECTS IN MATERIAL DISTRIBUTION IN TRANSPARENT CONTAINERS

The present invention relates to the technique field of optoelectronic inspection of containers of transparent or translucid character, such as bottles, pots or flasks, for detecting material distribution defects and in particular localised defects in thickness usually called defects of thin type.

The object of the invention is also to propose an inspection technique for determining the nature or type of material distribution defects presented by containers to rectify causes engendered by such defects.

In the technique field of glass container manufacturing, it is known that there is a risk of containers having one or more localised zones of poor material distribution affecting the aesthetics or worse still, the mechanical resistance of the containers. It is known that the defects of minimal thickness or «thin areas» form mainly in specific regions of the container and exhibit different radii of curvature such as the shoulder or the heel of the container. To detect such defects, it is known for example from patent EP 0 320 139 to measure the thickness of the container by sending a light beam to the wall of the container according to an angle such that part of the light beam is reflected by the external face of the wall and part of the beam is refracted in the wall then reflected by the internal face of the wall. The beams reflected by the internal and external faces of the wall are recovered by a Fresnel lens to be sent to a linear light sensor. The thickness of the wall of the container is measured as a function of separation, at the level of the light sensor, between the reflected beams by the internal and external faces of the wall.

The container is driven in rotation according to a turn for measuring its thickness according one of its transversal straight sections. Advantageously, the transversal inspection section is located in a zone of the container having a major risk of forming thin areas, such as the heel or the shoulder.

Document EP 0 871 007 describes a similar technique for measuring the thickness of the wall and/or the ovalisation of a container. In the same sense, document GB 2 195 278 describes a process for determining various particular physical features of a glass container such as the glass thickness, the irregularities and defects likely to appear in the container.

Analysis of former known solutions results in noting that none of them determines the nature or type of material distribution defects presented by the containers. In fact, the measurement taken is interpreted as corresponding to a type of defect, for example a thin area, whereas it corresponds in reality to another type of defect such as a parting line.

The present invention therefore aims to rectify the disadvantages of the prior art by proposing a novel inspection technique for reliably detecting material distribution defects likely to appear on transparent or translucid containers.

To attain such an aim, the inspection process according to the invention intends to detect material distribution defects in transparent containers having a central axis and a wall delimited between an external face and an internal face, the process consisting for a series of inspection points distributed over an inspection region on the one hand superposed according to a determined height of the container taken according to the central axis, and on the other hand according to the circumference of the container:
- of sending at least one light beam to the wall of the container following an angle such that part of the light beam is reflected by the external face of the wall and part of the beam is refracted in the wall then reflected by the internal face of the wall,
- recovering on a light sensor the reflected beams by the internal and external faces,
- measuring at each inspection point the thickness of the wall as a function of the separation at the level of the light sensor, between the reflected beams by the internal and external faces.

According to the invention, the process consists:
- of processing the thickness measurements by analysing their distribution over the inspection region to extract therefrom geometric characteristics and comparing these geometric characteristics to reference values to determine if the container has material distribution defect.

Another object of the invention is to propose a process for determining the type of material distribution defects presented by the containers.

To achieve such an aim, the process consists of comparing the geometric characteristics extracted from the thickness measurements to reference values corresponding to different types of material distribution defect to determine the type of material distribution defect presented by the container.

Also, the process according to the invention can also have in combination at least one and/or the other of the following additional characteristics:
- taking into account as geometric distribution characteristics of the thickness measurements, the surface, the length, the width, the orientation, the correctness, the amplitude and/or the slope,
- taking into account the geometric characteristics of the thickness measurements less than a critical thickness value to characterise the presence of a defect of thin type,
- taking into account the orientation and/or the correctness of the distribution of the thickness measurements to characterise the presence of a defect of offset parting line type,
- taking into account the orientation of the distribution of the thickness measurements to characterise a defect of bubble type by a localised localized and rapid variation of said distribution of thickness measurements,
- conduct inspection for a series of inspection points:
  - by sending a light beam in the form of a luminous line having a length determined according to the height of the container taken according to the vertical axis,
  - by selecting a series of inspection points according to the height of the container taken according to the vertical axis, so as to recover for each of them the reflected beams by the internal and external faces and measure the thickness of the wall,
  - by relatively displacing relative to the light sensor the container on one turn,
  - and by selecting a displacement incrementation pitch of the container so as to renew for each displacement incrementation pitch the operations for determining the thickness of the wall at different inspection points according to the height of the container,
- selecting between 3 and 50 inspection points according to the height of the container and preferably around 20 inspection points, according to an inspection pitch of between 0.02 and 5 mm and preferably around 1 mm according to the height of the container, with a displacement incrementation pitch of between 0.5 and 5 mm and preferably of the order of 1 mm according to the circumference of the container,
- selecting the inspection points according to the height of the container corresponding to an inspection zone to cover at least one connection zone of the wall having different radii of curvature such as the shoulder or the heel of the container, recovering the reflected beams by the external and internal faces, by means of a light sensor adapted to acquire a bi-dimensional image from which the thickness measurements at different points are made, sending a light beam having chromatic coding, recovering the reflected beams by the internal and external faces, on a sensor for analysing the wavelength of said reflected beams and determining the thickness as a function of the wavelengths of said reflected beams, filtering, interpolating or correcting signals delivered by the light sensor according to the vertical and/or horizontal direction of the light sensor and/or over time.

Another object of the invention is to propose installation for reliably detecting material distribution defects.

To attain such an aim, the inspection installation for detecting material distribution defects in transparent containers having a central axis and a wall delimited between an external face and an internal face, for executing the process comprises:

a light source for sending a light beam to the wall of the container, in the form of a luminous line having a length determined according to the height of the container taken according to the central axis, the light beam being sent according to an angle such that part of the light beam is reflected by the external face of the wall and part of the beam is refracted in the wall then reflected by the internal face of the wall, a light sensor capable of recovering the reflected beams by the internal and external faces, a system for relative displacement relative to the light sensor of containers according to the central axis, an acquisition and processing unit connected to the light sensor comprising means:

for selecting a series of inspection points distributed on the one hand superposed according to a determined height of the container taken according to the central axis, and on the other hand according to the circumference of the container, for measuring at each inspection point the thickness of the wall as a function of separation at the level of the light sensor, between the reflected beams by the internal and external faces, for processing the thickness measurements by analysing their distribution over the inspection region to extract geometric characteristics therefrom, for comparing these geometric characteristics to reference values for determining if the container has a material distribution defect.

Also, the installation according to the invention can also present in combination at least one and/or the other of the following additional characteristics:

the light sensor is a matrix camera connected to the acquisition and processing unit which ensures the acquisition of bidimensional images, the light sensor is a spectrometer for analysing the wavelengths of reflected beams on the internal and external faces and originating from a light beam having chromatic coding.

Various others characteristics will emerge from the following description in reference to the attached diagrams which show, by way of non-limiting examples, embodiments of the object of the invention.

Figure 1:
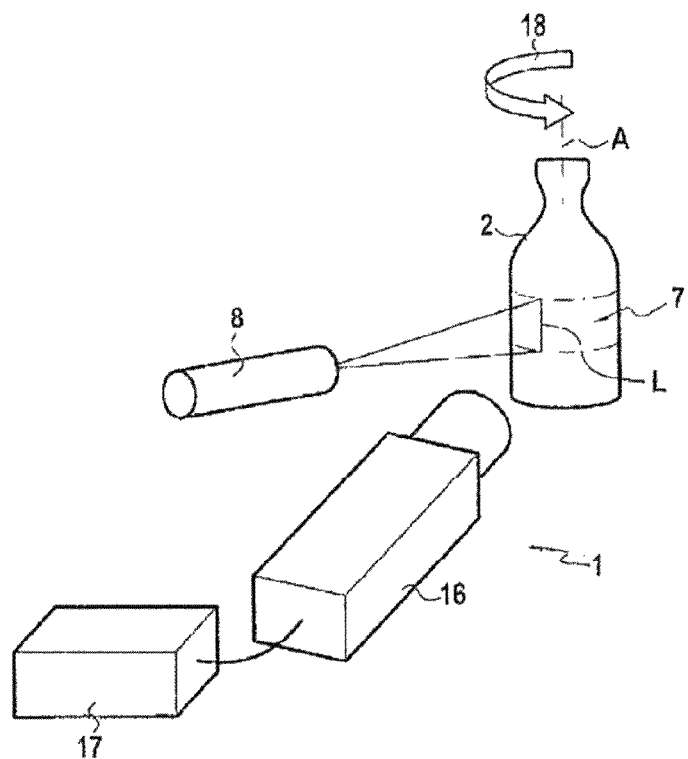
FIG. 1 is a schematic view of a first variant embodiment of an inspection installation according to the invention.
Figure 2:
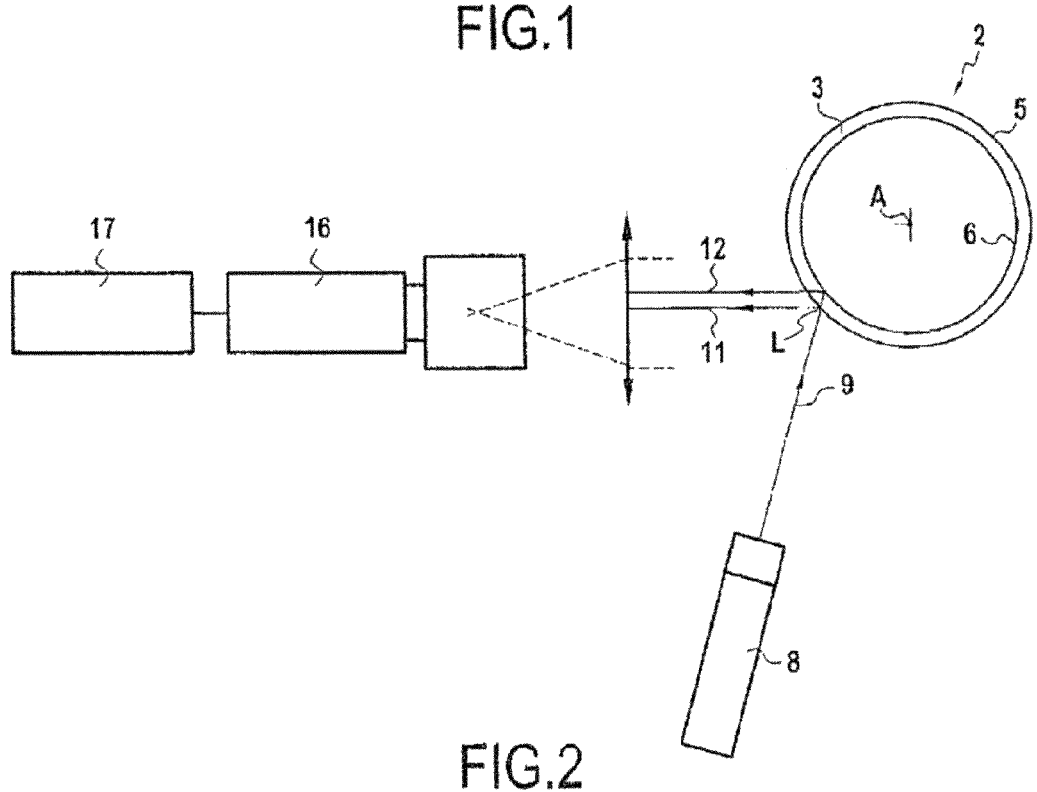
FIG. 2 is a schematic view showing in section the inspection of a container via the installation illustrated in FIG. 1.
Figure 3:
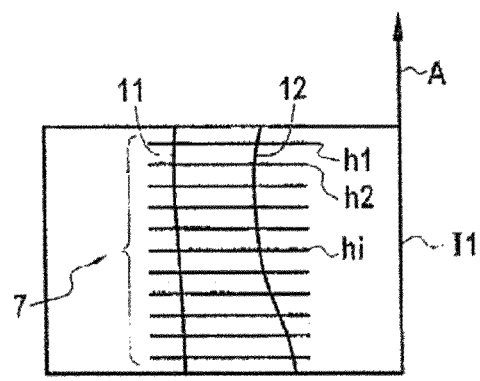
FIG. 3 is an image example obtained via the inspection installation illustrated in FIGS. 1 and 2.

FIGS. 1 to 3 illustrate a first exemplary embodiment of an installation 1 for detecting material distribution defects on transparent or translucid containers 2 having a central axis A. As is evident more precisely from FIG. 2, each container 2 has a wall of revolution 3 delimited between an external face 5 and an internal face 6.

In keeping with the invention, the installation 1 is adapted to detect material distribution defects in the wall 3 of containers 2. In the case of a glass container, the installation 1 aims to detect defects of poor distribution of the glass. In the main, the installation 1 detects a defect of thin type as material distribution defect. The installation 1 also detects as material distribution defect offset parting lines forming a wing, forming bubbles and refining bubbles (or chip), pins, folds, tears, granite glass skin, stuck to forceps.

Advantageously, the installation 1 is adapted for observing a zone or inspection region 7 extending over the entire circumference of the container and having a height taken according to the central axis A encompassing the entire zone in which thin areas are likely to appear as material distribution defect. The inspection region 7 extends according to a bidimensional surface. For example, the inspection region 7 corresponding to the heel or the shoulder of the container. The inspection region 7 extends over the entire circumference of the container, according to a height of between 0.5 and 50 mm and preferably of the order of 20 mm.

The installation 1 comprises a light source 8 adapted for sending a light beam 9 to the wall 3 of the container in the form of a luminous line L having a length determined according to the height of the container taken according to the central axis A. For example, the light source 8 is a laser. According to an advantageous characteristic of the invention, the length of the luminous line L taken according to the central axis A corresponds at least to the height of the inspection region 7.

The light beam 9 is sent according to an angle such that part 11 of the light beam 9 is reflected by the external face 5 and part 12 of the beam 9 is refracted in the wall 3 then reflected by the internal face 6 of the wall. As is evident more precisely from FIG. 2, sending the light beam 9 results in obtaining a beam reflected 11 by the external face 5 and a beam reflected 12 by the internal face 6.

The installation also comprises a light sensor 16 capable of recovering the reflected beams 11, 12 by the respectively external 5 and internal 6 faces. The light sensor 16 is advantageously a matrix camera for acquiring a bidimensional image of the inspection region 7. The camera 16 is connected to an acquisition and processing unit 17 for acquiring and processing images taken by the camera. The camera 16 and the acquisition and processing unit 17 are not described in greater detail since they are well known to the expert.

The inspection installation 1 also comprises a relative displacement system 18 for containers 2, relative to the light sensor 16 so as to allow inspection of containers according to its entire circumference, by taking successive images during relative displacement of containers. According to an advantageous variant embodiment, the displacement system 18 ensures rotation of containers about its central axis A on one turn. In the case of a form container, that is, not having a general cylindrical form, inspection is conducted over the entire circumference or perimeter of the container.

FIG. 3 illustrates an example of an image taken by the camera 16 for a determined angular position of the container relative to the camera. The image $I_1$ on the one hand displays the image of the beam reflected 11 by the external face 5 of the wall 3 and on the other hand the image of the beam reflected 12 by the internal face 6 of the wall 3. The images of the reflected beams 11, 12 appear on the image $I_1$ according to two luminous lines having a length according to the central axis A corresponding to the height of the inspection region 7 and apart from each other, according to a direction perpendicular to the central axis A by a distance corresponding to the thickness of the wall 3. The acquisition and processing unit 17 is adapted to take successive images of the wall 3 of the container 2 during rotation of the container 2 on one turn. In other terms, the acquisition and processing unit 17 takes two successive images for a determined rotation pitch of the container for example between 0.5 and 5 mm and preferably of the order of 1 mm according to the circumference of the container.

For each image taken, the acquisition and processing unit 17 selects a series of levels or inspection points $h_1, h_2, \ldots h_i$ distributed superposed according to the determined height of the container taken according to the central axis A.

For example, it is provided to select for the inspection region 7 between 3 and 50 inspection points $h_i$ according to the height of the container and preferably around 20 inspection points, according to an inspection pitch of between 0.02 and 5 mm and preferably about 1 mm. In the example illustrated in FIG. 3, 11 inspection points $h_i$ are taken according to the height of the container in the inspection region 7 equal to 20 mm. For each inspection point $h_i$, the acquisition and processing unit 17 determines the thickness of the wall 3 as a function of separation at the level of the image $I_1$ between the reflected beams 11, 12 by the internal 6 and external 5 faces. In other terms, for each level $h_i$ the thickness of the wall 3 is determined. In the example illustrated in FIG. 3, 11 thicknesses are determined in the image $I_1$ corresponding to each height or level $h_i$.

This operation for determining the thicknesses of the wall 3 in an image is repeated on the different images taken according to the entire circumference of the container 2. For this purpose, the container 2 is set in rotation about its central axis A on one turn. At each displacement incrementation pitch, specifically rotation in the example illustrated, of the container 2, the acquisition and processing unit 17 takes an image and determines the thicknesses of the wall 3 according to the different selected points or level of inspection $h_i$. Advantageously, the number and position of the inspection points remain identical from one image to the other. In the example illustrated, for each angular offset for example by 1 mm, the acquisition and processing unit 17 proceeds with measuring the thickness of the inspection region 7, according to the 11 determined levels $h_i$.

Figure 4:
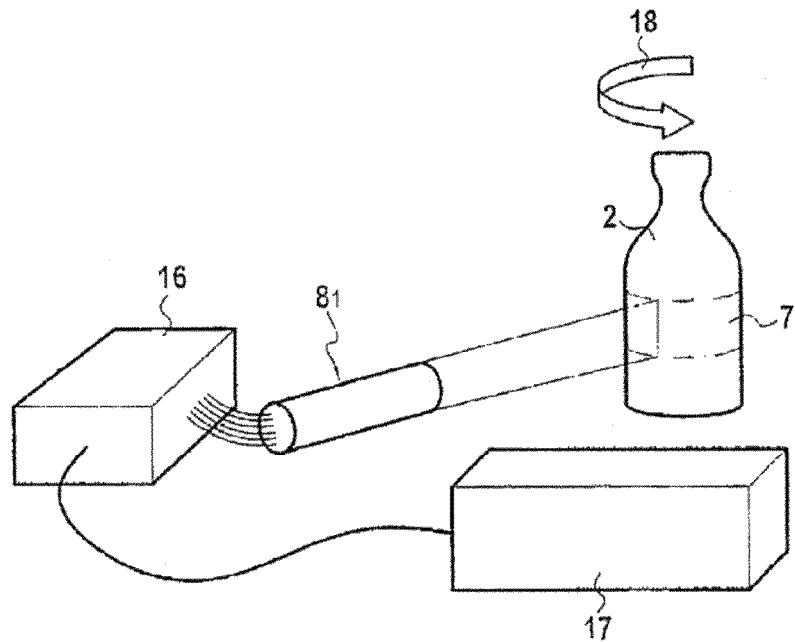
FIG. 4 is a schematic view showing another exemplary embodiment of an inspection installation according to the invention.

FIG. 4 illustrates another variant embodiment in which the light beam 9 sent to the container 2 has chromatic coding generated by at least one chromatic probe $8_1$, that is, the light beam 9 has different wavelengths of known and selected values, to allow detection of the thickness of the wall 3.

The light beam 9 which is formed by one or more elementary beams originating from one or more chromatic probes also has a determined height for covering the surface of the container in the inspection zone 7, as explained in relation to FIGS. 1 to 3. The light beam 9 is focussed on the wall 3 such that beams are reflected onto the internal 6 and external faces 5. The beams reflected by the internal 6 and external 5 faces are recovered by the chromatic probe $8_1$ and directed to a light sensor 16 such as a spectrometer for analysing the wavelengths of the reflected beams by the external 5 and internal 6 faces. As a function of the wavelengths of the reflected beams, the acquisition and processing unit 17 determines the thickness of the wall 3 at the different inspection points $h_i$, as explained hereinabove.

The acquisition and processing unit 17 processes the thickness measurements by searching to see if at least one of the thickness measurements determined at the various inspection points $h_i$ is less than a critical minimal thickness value. This critical minimal thickness value corresponds to the presence of a thin area. In the event where at least one thickness measurement is less than the critical minimal thickness value, the acquisition and processing unit 17 supplies a defect signal to point out that the container is defective.

According to an advantageous characteristic, the acquisition and processing unit 17 processes the thickness measurements by analysing the distribution of the thickness measurements less than a critical thickness value to determine if the container has a thin area as material distribution defect. Taking into account the thickness measurements according to both directions of the surface of the wall 3 gives an extra indication of the form of the defect noted.

According to a characteristic of the invention, the thickness measurements are processed by analysing their distribution over the inspection region 7 to extract therefrom geometric characteristics such as for example the surface, the length, the width, the orientation, the correctness, the amplitude and/or the slope. In fact, each type of material distribution defects, apart from the thin area, and such as the forming bubble, the offset parting line, the pin ( . . . ) has a «geometric signature».

Figure 5:
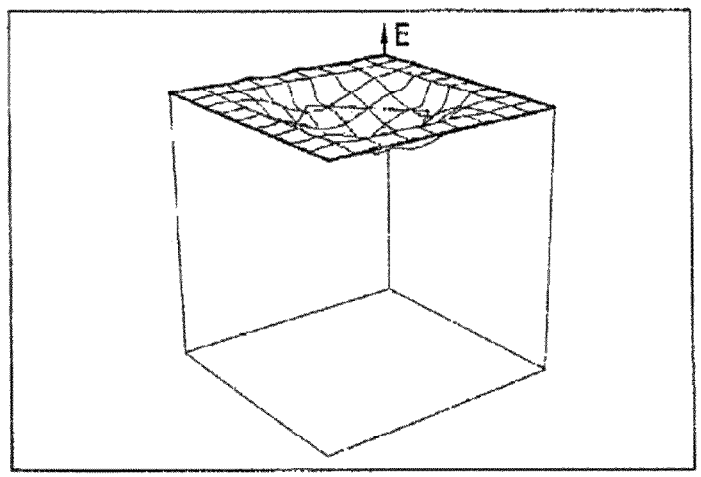
FIGS. 5 to 8 are figures illustrating different distributions of thickness corresponding to a defect respectively of thin area type, offset parting line, bubble and wing.
Figure 6:
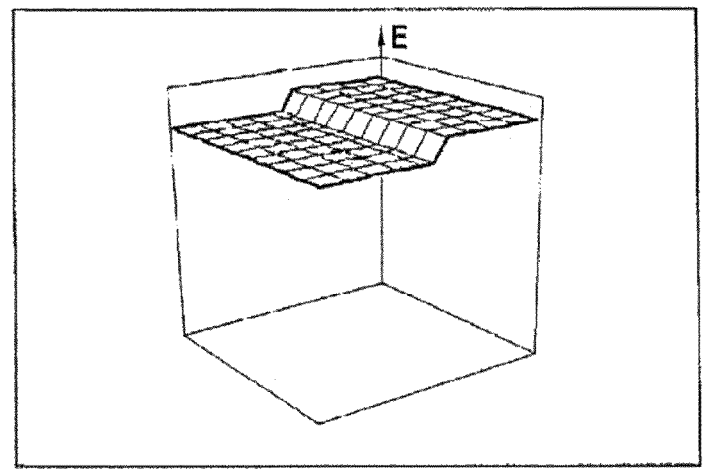
Figure 7:
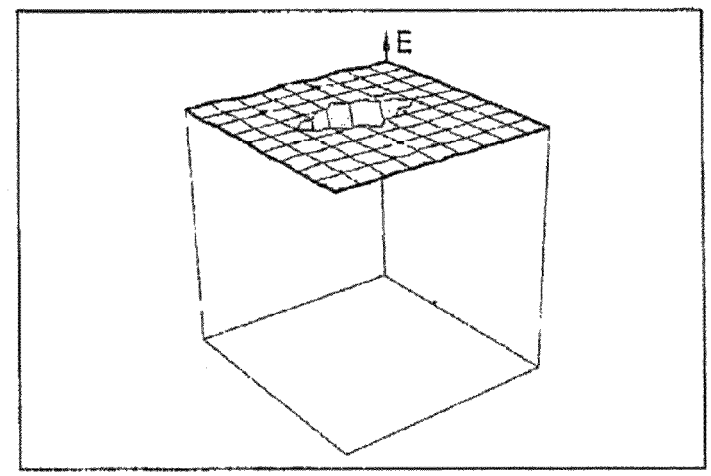

FIGS. 5 to 7 illustrate three examples of distribution of thickness measurements E in the inspection region 7, each having a geometric signature characteristic of a type of material distribution defect.

FIG. 5 illustrates a defect of poor thickness distribution, linked to a shaping problem of the container. Taking into account the geometric characteristics of the thickness measurements E in particular those less than a critical thickness value characterises the presence of a defect of thin type.

FIG. 6 illustrates a defect of offset parting line type whereof the geometric signature appears in the orientation and/or the correctness of the distribution of the thickness measurements E.

FIG. 7 illustrates a defect of bubble type whereof the geometric signature is characterised by localised and rapid variation of the distribution of the thickness measurements E.

Figure 8:
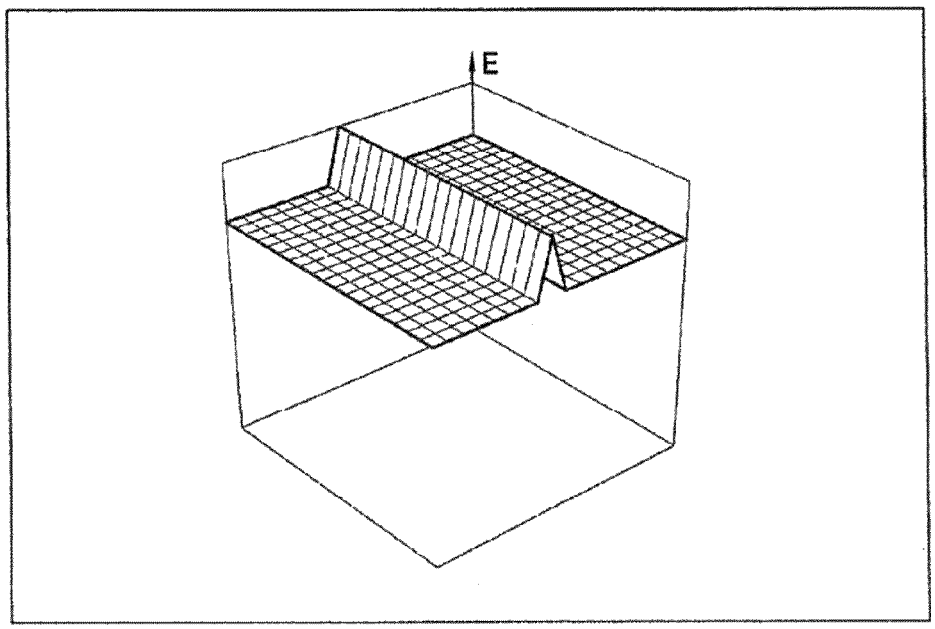

FIG. 8 illustrates a defect of wing type whereof the geometric signature is characterised by localised rapid and continuous variation of the distribution of the thickness measurements E.

Figure 9:
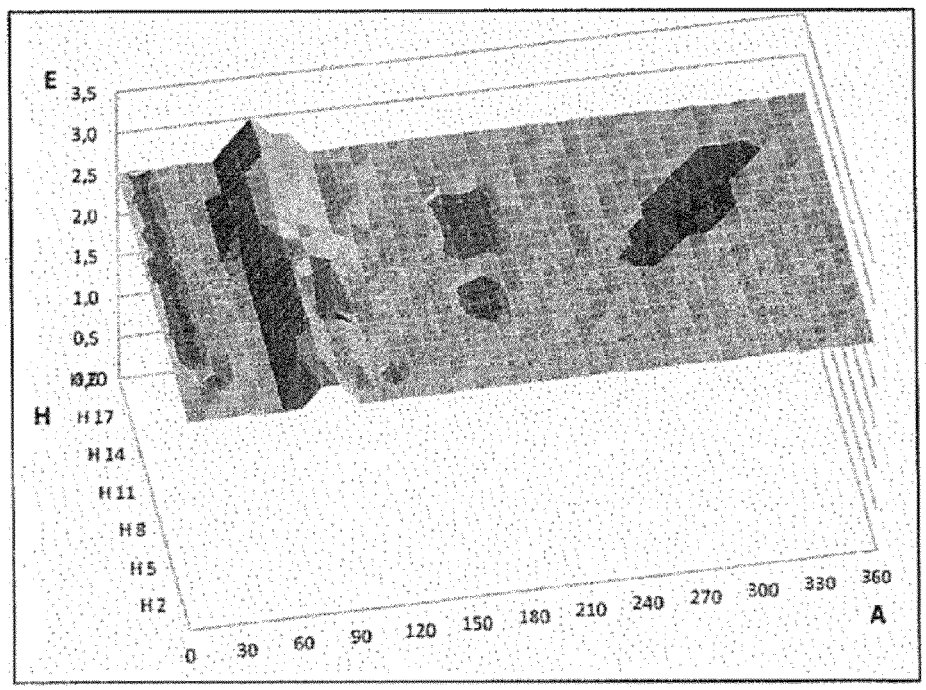
FIG. 9 is a representation of the distribution of thickness on a determined height and over 360° of a container.

FIG. 9 illustrates an example of distribution of thickness measurements E (mm) on a height H (mm) determined and according to the entire periphery A (°) of the container.

The geometric characteristics extracted from the distribution of the thickness measurements are compared to reference values corresponding to different types of material distribution defects known or ascertained. Such comparison determines whether the container reliably has a material distribution defect. According to a variant embodiment, such comparison identifies the type of material distribution defect presented by the container. Such identification of the type of material distribution defect addresses the causes having engendered this defect with a view to rectifying it.

To improve detection of the type of defect, the acquisition and processing unit 17 can also take into account the relative profiles of the external 5 and internal 6 faces from the images of the reflected beams 11, 12 appearing on the images taken by the camera 16.

The aim of the invention is to reliably detect the existence of a thin area by distinguishing it from other material distribution defects. Advantageously, this detection is conducted in a localised region extending over a surface of the container encompassing the entire zone in which a thin area is likely to form. Of course, it can be feasible to simultaneously inspect several zones of the same container.

Another advantage of the invention is during analysis of the signals delivered by the light sensors 16 to filter them according to both directions and apply algorithms and two-dimensional image-processing filters to detect the images of the reflected beams 11, 12 (FIG. 3). Such a filtering operation for example corrects the risks of the signal due to surface imperfections of the container.

Therefore, according to an advantageous variant embodiment the filtering operation can be conducted according to the measuring direction of the thickness.

In this respect, it should be noted that the abscissa of the image illustrated in FIG. 3 corresponds in the case of a measuring process based on triangulation to the abscissa of the linear or matrix light sensor. This abscissa depends on deviation of the beams reflected on the internal and external faces. The distance between the beams reflected on the two faces and therefore their abscissa spread determines the thickness. FIG. 3 can be considered as a matrix image even when the light sensor is a set of superposed linear image sensors.

In the case of a measuring process based on chromatic coding (FIG. 4), the abscissa of the image illustrated in FIG. 3 corresponds to a wavelength. The measuring principle is in fact chromatic coding obtained by focussing a multitude of polychromatic accurate sources (or a slot) by means of a strongly chromatic lens. The reflected beams on the internal and external faces are not the same dominant colour. After filtering of pinhole or slot type, a monochromator horizontally distributes the beams on a series of superposed linear sensors or else a matrix sensor. FIG. 3 therefore illustrates an aspect very similar to the triangulation system, considering that the abscissas are wavelengths.

Of course, at all stages of analysis it seems possible to filter, interpolate or correct the signals delivered by the light sensor 16 according to the vertical and/or horizontal direction of the light sensor, and/or over time. As the acquisition of signals delivered by the light sensor is completed for each rotation increment of the container, filtering according to time returns to filtering according to the angle of rotation, that is, according to the circumference of the container.

The invention is not limited to the examples described and represented since various modifications can be made without departing from its scope.

The invention claimed is:

1. An inspection process for detecting material distribution defects in transparent containers (2) having a central axis (A) and a wall (3) delimited between an external face (5) and an internal face (6), the process comprising for a series of inspection points distributed over an inspection region (7) superposed along a determined height of the container taken according to the central axis (A), and along the circumference of the container ($h_i$):

sending at least one light beam (9) to the wall of the container following an angle such that part (11) of the light beam is reflected by the external face (5) of the wall and part (12) of the beam is refracted in the wall then reflected by the internal face (6) of the wall, recovering on a light sensor (16) the reflected beams (12, 11) by the internal (6) and external (5) faces, measuring at each inspection point ($h_i$) the thickness of the wall (3) as a function of separation at the level of the light sensor (16) between the reflected beams by the internal and external faces, characterized in that it consists of:

processing the thickness measurements by analyzing their distribution over the inspection region (7) to extract therefrom geometric characteristics, and comparing these geometric characteristics to reference values to determine if the container has a material distribution defect, taking into account, as geometric distribution characteristics of the thickness measurements, one or more of the surface, the length, the width, the orientation, the correctness, and the slope of the material distribution effects and comparing the geometric characteristics extracted from the thickness measurements to reference values corresponding to different types of material distribution defect to determine the type of material distribution defect presented by the container.

2. The inspection process as claimed in claim 1, characterized by taking into account the geometric characteristics of the thickness measurements less than a critical thickness value to characterise the presence of a defect of thin type.

3. The inspection process as claimed in claim 1, characterized by taking into account one or more of the orientation and the correctness of the distribution of the thickness measurements to characterise the presence of a defect of offset parting line type.

4. The inspection process as claimed in claim 1, characterized by taking into account the orientation of the distribution of the thickness measurements to characterize a defect of bubble type by localized and rapid variation of said distribution of the thickness measurements.

5. The inspection process as claimed in claim 1, characterized by conducting the inspection for a series of inspection points ($h_i$):

by sending a light beam (9) in the form of a luminous line having a determined length along the height of the container taken according to the vertical axis (A), by selecting a series of inspection points ($h_i$) along the height of the container taken according to the vertical axis (A), so as to recover for each of them the reflected beams by the internal (6) and external (5) faces and measuring the thickness of the wall, by displacing the container (2) relatively relative to the light sensor (16) by one turn, and by selecting a relative displacement incrementation pitch of the container (2) such as to, for each displacement incrementation pitch, renew operations aiming to determine the thickness of the wall (3) at different inspection points ($h_i$) along the height of the container.

6. The inspection process as claimed in claim 1, characterized in that the process comprises selecting between 3 and 50 inspection points ($h_i$) along the height of the container, preferably about 20 inspection points, according to an inspection pitch of between 0.02 and 5 mm, preferably about 1 mm along the height of the container, an according to an incrementation pitch of between 0.5 and 5 mm, preferably of the order of 1 mm along the circumference of the container.

7. The inspection process as claimed in claim 1, characterized by selecting the inspection points ($h_i$) along the height of the container corresponding to an inspection zone (7) to cover at least one connection zone of the wall (3) having different radii of curvature such as the shoulder or the heel of the container.

8. The inspection process as claimed in claim 1, characterized by recovering the reflected beams (12, 11) by the external (5) and internal (6) faces by means of a light sensor (16) adapted to acquire a bi-dimensional image from which the thickness measurements at different points ($h_i$) are made.

9. The inspection process as claimed in claim 1, characterized by sending a light beam having chromatic coding, recovering the reflected beams by the internal (5) and external (6) faces on a sensor for analyzing the wavelength of said reflected beams, and determining the thickness as a function of the wavelengths of said reflected beams.

10. The inspection process as claimed in claim 1, characterized by filtering, interpolating or correcting the signals delivered by the light sensor (16) according to one or more of the vertical and horizontal direction of one or more of the light sensor and over time.

11. Inspection installation for detecting material distribution defects in transparent containers (2) having a central axis (A) and a wall (3) delimited between an external face (5) and an internal face (6), for executing the process as claimed in claim 1, characterized in that the installation comprises:
  a light source (8) for sending a light beam (9) to the wall (3) of the container, in the form of a luminous line (L) having a length determined according to the height of the container taken according to the central axis (A), the light beam being sent according to an angle such that part of the light beam is reflected by the external face of the wall and part of the beam is refracted in the wall then reflected by the internal face of the wall,
  a light sensor (16) capable of recovering the reflected beams by the internal (6) and external (5) faces,
  a relative displacement system (18) relative to the light sensor (16) of the containers,
  an acquisition and processing unit (17) connected to the light sensor (16):
    for selecting a series of inspection points ($h_i$) distributed along a determined height of the container taken according to the central axis (A), and along the circumference of the container,
    for measuring at each inspection point ($h_i$) the thickness of the wall as a function of separation at the level of the light sensor (16) between the reflected beams by the internal (6) and external (5) faces,
    for processing the thickness measurements by analyzing their distribution over the inspection region (7) to extract therefrom geometric characteristics, to compare these geometric characteristics to reference values to determine if the container has a material distribution defect.

12. The installation as claimed in claim 10, characterized in that the light sensor (16) is a matrix camera connected to the acquisition and processing unit which ensures the acquisition of bi-dimensional images.

13. The installation as claimed in claim 10, characterized in that the light sensor (16) is a spectrometer for analyzing the wavelengths of the reflected beams on the internal (6) and external (5) faces and originating from a light beam having chromatic coding.

14. An inspection process for detecting material distribution defects in transparent containers (2) having a central axis (A) and a wall (3) delimited between an external face (5) and an internal face (6), the process comprising, for a series of inspection points ($h_i$) distributed over an inspection region (7) superposed along a determined height of the container taken according to the central axis (A), and along the circumference of the container:
  sending at least one light beam (9) to the wall of the container following an angle such that part (11) of the light beam is reflected by the external face (5) of the wall and part (12) of the beam is refracted in the wall then reflected by the internal face (6) of the wall,
  recovering on a light sensor (16) the reflected beams (12, 11) by the internal (6) and external (5) faces,
  measuring at each inspection point ($h_i$) the thickness of the wall (3) as a function of separation at the level of the light sensor (16) between the reflected beams by the internal and external faces,
characterized in that it consists of:
  processing the thickness measurements by analyzing the distribution of the thickness measurements less than a critical thickness value to determine if the container has a thin area as material distribution defect, taking into account the thickness measurements according to both directions of the surface of the wall 3 over the inspection region (7), to extract therefrom geometric characteristics, and comparing these geometric characteristics to reference values to determine if the container has a material distribution defect.

15. The inspection process as claimed in claim 14, characterized by comparing the geometric characteristics extracted from the thickness measurements to reference values corresponding to different types of material distribution defect to determine the type of material distribution defect presented by the container.

16. The inspection process as claimed in claim 14, characterized by taking into account as geometric distribution characteristics of the thickness measurements, one or more of the surface, the length, the width, the orientation, the correctness, the amplitude and the slope.

17. The inspection process as claimed in claim 14, characterized by taking into account as geometric distribution characteristics of the thickness measurements, the surface of the material distribution defect.

18. The inspection process as claimed in claim 17, characterized by conducting the inspection for a series of inspection points ($h_i$):
  by sending a light beam (9) in the form of a luminous line having a determined length along the height of the container taken according to the vertical axis (A),
  by selecting a series of inspection points ($h_i$) along the height of the container taken according to the vertical axis (A), so as to recover for each of them the reflected beams by the internal (6) and external (5) faces and measuring the thickness of the wall,
  by displacing the container (2) relative to the light sensor (16) by one turn,
  and by selecting a relative displacement incrementation pitch of the container (2) such as to, for each displacement incrementation pitch, renew operations aiming to determine the thickness of the wall (3) at different inspection points ($h_i$) along the height of the container.

19. The inspection process as claimed in any one of claim 17, characterized by selecting the inspection points ($h_i$) along to the height of the container corresponding to an inspection zone (7) to cover at least one connection zone of the wall (3) having different radii of curvature such as the shoulder or the heel of the container.

20. The inspection process as claimed in any one of claim 17, characterized by recovering the reflected beams (12, 11) by the external (5) and internal (6) faces by means of a light sensor (16) adapted to acquire a bi-dimensional image from which the thickness measurements at different points ($h_i$) are made.

21. The inspection process as claimed in claim 17, characterized by sending a light beam having chromatic coding, recovering the reflected beams by the internal (5) and external (6) faces on a sensor for analyzing the wavelength of said reflected beams, and determining the thickness as a function of the wavelengths of said reflected beams.

22. The inspection process as claimed in claim 1, characterized in that processing the thickness measurements by analyzing their distribution over the inspection region (7) takes into account, as geometric distribution characteristics of the thickness measurements, at least the surface of the material distribution defect.

* * * * *